(12) United States Patent
Huang et al.

(10) Patent No.: US 10,682,329 B2
(45) Date of Patent: *Jun. 16, 2020

(54) ENTACAPONE FOR TREATMENT OF OBESITY

(71) Applicant: National Institute of Biological Sciences, Beijing, Beijing (CN)

(72) Inventors: Niu Huang, Beijing (CN); Gang Zhi, Beijing (CN); Jijie Chai, Beijing (CN); Shiming Peng, Beijing (CN); Nannan Hou, Beijing (CN)

(73) Assignee: National Institute of Biological Sciences, Beijing, Beijing (CN)

(*) Notice: Subject to any disclaimer, the term of this patent is extended or adjusted under 35 U.S.C. 154(b) by 35 days.

This patent is subject to a terminal disclaimer.

(21) Appl. No.: 16/018,095

(22) Filed: Jun. 26, 2018

(65) Prior Publication Data

US 2018/0303788 A1   Oct. 25, 2018

Related U.S. Application Data

(63) Continuation of application No. 14/147,531, filed on Jan. 4, 2014, now Pat. No. 10,004,715, which is a continuation of application No. PCT/CN2013/087581, filed on Nov. 21, 2013.

(30) Foreign Application Priority Data

Nov. 28, 2012  (CN) .......................... 2012 1 0497436

(51) Int. Cl.
*A61K 31/277* (2006.01)
*A61K 45/06* (2006.01)
*C12Q 1/6883* (2018.01)

(52) U.S. Cl.
CPC ............ *A61K 31/277* (2013.01); *A61K 45/06* (2013.01); *C12Q 1/6883* (2013.01); *C12Q 2600/156* (2013.01)

(58) Field of Classification Search
CPC .................................................. A61K 31/277
See application file for complete search history.

(56) References Cited

U.S. PATENT DOCUMENTS 10,004,715 B2 * 6/2018 Huang ................. A61K 31/277
2008/0249156 A1 * 10/2008 Palepu ................. A61K 31/337
                                                    514/423
2013/0131127 A1 * 5/2013 Chen ................... A61K 31/4245
                                                    514/364

OTHER PUBLICATIONS

Frayling et al., Science, 2007, 316(5826): 889-94.*
Price et al. BMC Med Genet, 2008, 9:4 (abstract).*
Entacapone (oral Route), 2012.*

* cited by examiner

*Primary Examiner* — Rei Tsang Shiao
(74) *Attorney, Agent, or Firm* — Richard Aron Osman

(57) ABSTRACT

Obesity is inhibited by administering to a person in need thereof an effective amount of entacapone ((2E)-2-cyano-3-(3,4-dihydroxy-5-nitrophenyl)-N,N-diethylprop-2-enamide), or a pharmaceutically-acceptable salt thereof, particularly in conjunction with a second, different anti-obesity medicament. Pharmaceutical compositions comprise entacapone copackaged or coformulated with a second, different anti-obesity medicament.

15 Claims, 4 Drawing Sheets

ENTACAPONE FOR TREATMENT OF OBESITY

CROSS-REFERENCE TO RELATED APPLICATIONS

This application is a continuation of Ser. No. 14/147,531, filed Jan. 4, 2014 (U.S. Ser. No. 10/004,715), which is a continuation of PCT/CN2013/087581, filed: Nov. 21, 2013, which claims priority to CN 2012-10497436.7, filed Nov. 28, 2012.

INTRODUCTION

Obesity is becoming a severe health problem worldwide and many factors contribute to this chronic disease, including environmental factors and genetic factors. Recently, GWAS (genome-wide association studies) were applied to investigate patients with obesity and a single gene—FTO (fat mass and obesity) was identified to strongly associate with obesity.[1-4] FTO's functional role in obesity was subsequently confirmed in transgenetic animal models, such as FTO knockout mouse, FTO-overexpression mouse and FTO-I367F mutation mouse.[5-8] More specifically, FTO global-knockout and neuron-specific knockout induce body weight loss[5,6], while FTO gene overexpression results in obesity.[8] One mis-sense mutation was observed to inhibit FTO enzymatic function and protect mouse from obesity.[7] Nevertheless, FTO is expressed in many tissues, especially in hypothalamic nuclei controlling energy expenditure,[9] which is consistent with the suggestion that FTO affects energy homeostasis.[6]

FTO protein is an α-ketoglutarate and iron (II) dependent nucleic acid demethylase.[9,10] Its preferred substrate is $N^6$-meA in message RNA, which locates near the stop codon and influences gene translation.[11,12] However, its mode of mechanism is not clear, such as its upstream and downstream effectors and its regulation mechanism. It is desirable to identify small molecule, drug-like FTO inhibitors for studying FTO function and discovering novel anti-obesity agent.

Existing drugs are approved for human use and have known safety profiles, so they can be rapidly evaluated for new indications of biological interest. Herein, we report the identification of a known FDA approved drug—Entacapone as FTO inhibitor using structure-based virtual screening method in combination with biological activity measurements, including enzymatic activity, cellular activity and in high-fat diet induced obesity (DIO) animal model.

SUMMARY OF THE INVENTION

The invention provides methods and composition for inhibiting weight gain, wherein the methods are also applicable to promoting weight loss, reducing serum LDL, cholesterol, LDL-c, and/or triglycerides, and/or treating an obesity related or metabolic disease or ameliorating or reducing the pathology or severity of an obesity related or metabolic disease or a symptom of an obesity related or metabolic disease selected from diabetes, hyperglycemia, diabetic nephropathy, hyperlipemia, coronary heart disease, atherosclerosis, hypertension, cardiovascular or cerebrovascular diseases, or liver, kidney or thyroid diseases.

In one aspect the invention provides methods of inhibiting weight gain, promoting weight loss, reducing serum LDL, cholesterol, LDL-c, or triglycerides, or treating atherosclerosis, comprising administering to a person in need thereof an effective amount of entacapone ((2E)-2-cyano-3-(3,4-dihydroxy-5-nitrophenyl)-N,N-diethylprop-2-enamide), or a pharmaceutically-acceptable salt thereof.

In another aspect the invention provides methods of inhibiting weight gain comprising administering to a person in need thereof an effective amount of entacapone in conjunction with one or more different medicaments for inhibiting weight gain, promoting weight loss, reducing serum LDL, cholesterol, LDL-c, or triglycerides, or treating atherosclerosis.

In particular embodiments thereof, the person meets one or more criteria, such as (a) is not diagnosed with Parkinson's disease; (b) is less than 50, 40 or 30 years old; (c) is obese or over-weight; (d) suffers from or is diagnosed with an obesity related disease selected from diabetes, hyperglycemia, diabetic nephropathy, hyperlipemia, coronary heart disease, atherosclerosis, hypertension, cardiovascular or cerebrovascular diseases, or liver, kidney or thyroid diseases; (e) has genotype: SNP rs7202116 (G), rs1421085 (C), or rs9939609 (A); and/or (f) pathogenically expresses or over-expresses FTO or Fto.

In particular embodiments the method further comprising detecting in the person one or more of the criteria, particularly genotype SNP rs7202116 (G), or over-expression of FTO or Fto.

In particular embodiments the method further comprises detecting a resultant inhibition of weight gain, promotion of weight loss, and/or improvement or amelioration of one or more of the criteria.

In particular embodiments, the method further comprises administering to the person an effective amount of one or more additional, different medicaments for inhibiting weight gain, promoting weight loss, reducing serum LDL, cholesterol, LDL-c, or triglycerides, or treating atherosclerosis, particularly wherein the entacapone and medicament(s) are copackaged, coformulated or coadministered.

In another aspect the invention provides pharmaceutical compositions comprising entacapone copackaged or coformulated with one or more of the additional, different medicaments for inhibiting weight gain, promoting weight loss, reducing serum LDL, cholesterol, LDL-c, or triglycerides, or treating atherosclerosis.

In particular embodiments the subject methods and compositions employ entacapone dosages of 0.25-5 g, or g/day, or 0.5-5 g, or g/day.

The invention encompasses all combination of the particular embodiments recited herein.

DESCRIPTION OF PARTICULAR EMBODIMENTS OF THE INVENTION

Figure 1:
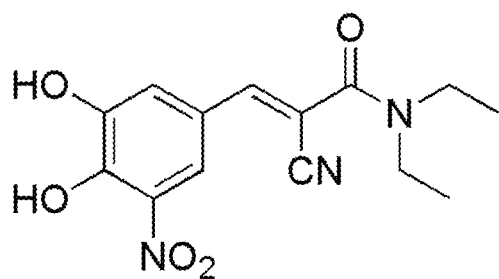
FIG. 1. The chemical structure of entacapone.

In one aspect the invention provides methods of inhibiting weight gain or promoting weight loss comprising administering to a person in need thereof an effective amount of entacapone ((2E)-2-cyano-3-(3,4-dihydroxy-5-nitrophenyl)-N,N-diethylprop-2-enamide), or a pharmaceutically-acceptable salt thereof, and including stereoisomers, particularly E-Z isomers, including polymeric forms, particularly the A form of the E isomer (e.g. U.S. Pat. No. 5,135,950).

The subject methods and compositions are also applicable to related indications: promoting weight loss, reducing serum LDL, cholesterol, LDL-c, and/or triglycerides, and/or treating an obesity related disease or ameliorating or reducing the pathology or severity of an obesity related disease or a symptom of an obesity related disease selected from diabetes, hyperglycemia, diabetic nephropathy, hyperlipemia, coronary heart disease, atherosclerosis, hypertension, cardiovascular or cerebrovascular diseases, or liver, kidney or thyroid diseases. Accordingly, the invention provides methods and compositions wherein entacapone is copackaged, coformulated or coadministered with one or more different medicaments for, specific for, or indicated for these related indications, and the methods may further comprising detecting, determining or diagnosing in the person one or more of the indications, and/or detecting a resultant improvement or amelioration of corresponding condition or symptom in the person.

In one aspect the invention provides methods of inhibiting weight gain comprising administering to a person in need thereof an effective amount of entacapone in conjunction with one or more different medicaments for inhibiting weight gain, promoting weight loss, reducing serum LDL, cholesterol, LDL-c, or triglycerides, or treating atherosclerosis, particularly wherein the entacapone and medicament(s) are copackaged, coformulated or coadministered.

Preferred different medicaments for these indications include different anti-weight gain medicaments, particularly a food intake inhibitor and/or a food absorption inhibitor; particularly Orlistat, Sibutramine, Lorcaserin, Rimonabant, Metformin, Exenatide, Pramlintide, or a pharmaceutically-acceptable salt thereof, and cholesterol lowering drugs, such as statins, including atorvastatin (Lipitor), fluvastatin (Lescol), lovastatin (Altoprev, Mevacor), pravastatin (Pravachol), rosuvastatin (Crestor), simvastatin (Zocor), or a pharmaceutically-acceptable salt thereof.

In particular embodiments thereof, the person meets one or more criteria indicative of the disclosed non-Parkinson's indication, and the method may further comprising detecting in the person one or more of the criteria, and/or detecting a resultant inhibition of weight gain, promotion of weight loss and/or improvement or amelioration of one or more of such criteria.

Criteria indicative of the disclosed non-Parkinson's indication include wherein the person (a) is not suffering from, or is not diagnosed with Parkinson's disease or symptoms thereof or other prior indication for entacapone or is not suffering from, or is not diagnosed with any degenerative disease of the central nervous system; (b) is less than 50, 40 or 30 years old; (c) is over-weight (e.g. a BMI of 25-30) or obese (e.g. a BMI of over 30); (d) suffers from, or is diagnosed with an obesity related disease selected from diabetes, hyperglycemia, diabetic nephropathy, hyperlipemia, coronary heart disease, atherosclerosis, hypertension, cardiovascular or cerebrovascular diseases, or liver, kidney or thyroid diseases; or (e) has a genotype associated with obesity or pathogenic or medically-undesirable weight gain, such as SNP rs7202116 (G), rs1421085 (C), or rs9939609 (A), or a surrogate or proxy SNP in linkage disequilibrium therewith (with respect to the correlative phenotype; see references below) and having a $r^2$ value greater than 0.5; and/or (f) pathogenically expresses or over-expresses FTO or Fto (e.g. comprises and expresses a multi-copy fto gene). Re rs7202116 G, see e.g. Yang et al., FTO genotype is associated with phenotypic variability of body mass index, Nature, Sep. 16, 2012, doi: 10.1038/nature11401 [epub]; re rs9939609 A, see e.g. Freathy R M, et al (2008). "Common variation in the FTO gene alters diabetes-related metabolic traits to the extent expected, given its effect on BMI". Diabetes 57 (5): 1419-26. doi: 10.2337/db07-1466. PMC 3073395. PMID 18346983; re rs1421085 C, see e.g. Dina C, et al., (2007). "Variation in FTO contributes to childhood obesity and severe adult obesity". Nature Genetics 39 (6): 724-6. doi:10.1038/ng2048. PMID 17496; and for multi-copy fto gene mouse, see e.g. Church et al., Overexpression of Fto leads to increased food intake and results in obesity, Nature Genetics, published online 14 Nov. 2010, doi:10.1038/ng.713.

In particular embodiments the person does not suffer from a pathogenic deficiency of L-DOPA (L-3,4-dihydroxyphenylalanine), does not indicate L-DOPA, and/or is not in need of L-DOPA (levopoda) or a dopaminergic agent, and/or the entacapone is not administered in conjunction with L-DOPA or a doaminergic agent.

In particular embodiments, the method further comprises administering to the person an effective amount of one or more additional, different medicament for inhibiting weight gain, promoting weight loss, reducing serum LDL, cholesterol, LDL-c, or triglycerides, or treating atherosclerosis, particularly wherein the entacapone and medicament(s) are copackaged, coformulated or coadministered.

In another aspect the invention provides pharmaceutical compositions comprising entacapone copackaged or coformulated with one or more of the additional, different medicaments for inhibiting weight gain, promoting weight loss, reducing serum LDL, cholesterol, LDL-c, or triglycerides, or treating atherosclerosis, particularly different anti-weight gain medicaments. For example, the entacapone and additional, different anti-weight gain medicaments may be coformulated, particularly in unit dosage form, or unit dosage forms of each may be copackaged in a multipack adapted for sequential use, such as blisterpack, comprising sheets of unit dosage forms. Exemplary coformulation and copackagings are shown in Table 2.

TABLE 2

Exemplary coformulation and copackagings.

1. Entacapone/Orlistat in 1000 mg/120 mg or 2000 mg/120 mg coformulated tablets.
2. Entacapone/Sibutramine in 1000 mg/10 mg or 2000 mg/10 mg coformulated tablets.
3. Entacapone/Lorcaserin in 1000 mg/10 mg or 2000 mg/10 mg coformulated tablets.
4. Entacapone/Rimonabant in 1000 mg/20 mg or 2000 mg/20 mg coformulated tablets.
5. Entacapone/Metformin in 1000 mg/500 mg or 2000 mg/500 mg coformulated tablets.
6. Entacapone/Exenatide: 1000 mg or 2000 mg tablet/250 mcg/mL solution (Byetta), copackaged
7. Entacapone/Exenatide: 1000 mg or 2000 mg tablet/suspension powder, ER 2 mg (Bydureon), copackaged
8. Entacapone/Pramlintide: 1000 mg or 2000 mg tablet/600 mcg/mL (as acetate), copackaged
9. Entacapone/Phentermine in 1000 mg/10 mg or 2000 mg/10 mg coformulated tablets.
10. Entacapone/atorvastatin (Lipitor) in 1000 mg/10 mg coformulated tablets.
11. Entacapone/fluvastatin (Lescol) in 1000 mg/80 mg coformulated tablets.
12. Entacapone/lovastatin (Altoprev, Mevacor) in 1000 mg/10 mg coformulated tablets.
13. Entacapone/pravastatin (Pravachol) in 1000 mg/10 mg coformulated tablets.
14. Entacapone/rosuvastatin (Crestor) in 1000 mg/5 mg coformulated tablets.
15. Entacapone/simvastatin (Zocor) in 1000 mg/10 mg coformulated tablets.
16. Entacapone/cholestyramine (Prevalite, Questran) in 1000/5000 mg copackaged powder.
17. Entacapone/colesevelam (Welchol) in 1000 mg/625 mg coformulated tablets.
18. Entacapone/colestipol (Colestid) in 1000 mg/1000 mg coformulated tablets.
19. Entacapone/ezetimibe (Zetia) in 1000 mg/10 mg coformulated tablets.
20. Entacapone/ezetimibe-simvastatin (Vytorin) in 1000/10/10 mg coformulated tablets.
21. Entacapone/fenofibrate (Lofibra, TriCor) in 1000 mg/54 mg coformulated tablets.
22. Entacapone/gemfibrozil (Lopid) in 1000 mg/600 mg coformulated tablets.
23. Entacapone/Niacin (Niaspan) in 1000 mg/500 mg coformulated tablets.
24. Entacapone/Omega-3 fatty acid (Lovaza) 1000 mg/4 mg coformulated tablets.

By targeting different pathways the coadmininistered drugs can act supplementally or synergistically to increase the potency compared with separate administration, and thereby also permit use reduced or otherwise suboptimal or subtherapeutic dosages, if not coadministered, while maintaining efficacy, such as 50%/50% and 25%/25% coformulations and copackagings of those shown in Table 2.

The term "pharmaceutically acceptable salts" is meant to include salts of the active compounds which are prepared with relatively nontoxic acids or bases, depending on the particular substituents found on the compounds described herein. When compounds of the invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, oxalic, maleic, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like. Certain specific compounds of the invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the invention.

In addition to salt forms, the compounds may be in a prodrug form. Prodrugs of the compounds are those compounds that undergo chemical changes under physiological conditions to provide the compounds of the invention. Additionally, prodrugs can be converted to the compounds of the invention by chemical or biochemical methods in an ex vivo environment. For example, prodrugs can be slowly converted to the compounds of the invention when placed in a transdermal patch reservoir with a suitable enzyme or chemical reagent. Prodrugs are often useful because, in some situations, they may be easier to administer than the parent drug. They may, for instance, be more bioavailable by oral administration than the parent drug. The prodrug may also have improved solubility in pharmacological compositions over the parent drug. A wide variety of prodrug derivatives are known in the art, such as those that rely on hydrolytic cleavage or oxidative activation of the prodrug. An example, without limitation, of a prodrug would be a compound of the invention which is administered as an ester (the "prodrug"), but then is metabolically hydrolyzed to the carboxylic acid, the active entity.

Subject compounds can exist in unsolvated forms as well as solvated forms, including hydrated forms. In general, the solvated forms are equivalent to unsolvated forms and are intended to be encompassed within the scope of the invention. Subject compounds may exist in multiple crystalline or amorphous forms. In general, all physical forms are equivalent for the uses contemplated and are intended to be within the scope of the invention.

Certain subject compounds possess asymmetric carbon atoms (optical centers) or double bonds; the racemates, diastereomers, geometric isomers and individual isomers are all intended to be encompassed within the scope of the invention.

The compositions for administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampules or syringes of the liquid compositions or pills, tablets, capsules, losenges or the like in the case of solid compositions.

A wide variety of suitable formulations and delivery systems, including suitable excipients or carriers and methods for preparing administrable compositions, are known or apparent to those skilled in the art and are described in more detail in such publications as *Remington: The Science and Practice of Pharmacy* (Pharmaceutical Press (2012). For example, in particular embodiments the compositions are formulated or delivered in extended or controlled delivery systems, such as diffusion systems (e.g. reservoir devices, matrix devices, diffusion-controlled implants and transdermal patches) and encapsulated and matrix dissolution systems, erosion products, osmotic pump systems, ion exchange resins, etc.

In particular embodiment the amount administered is far in excess of, at least 2, 2.5, 5 or 10× that (200 mg) currently indicated for Parkinson's Disease, and will preferably be 0.5-10, 0.5-5, 0.5-2.5, 1-10, 1-5, 1-2.5, 2-10, or 2-5 g/day, in unit dosage forms of 0.25, 0.5, 1, 1.5, 2 or 2.5 g.

The compounds can be administered by a variety of methods including, but not limited to, parenteral, topical, oral, or local administration, such as by aerosol or transdermally, for prophylactic and/or therapeutic treatment. Also, in accordance with the knowledge of the skilled clinician, the therapeutic protocols (e.g., dosage amounts and times of administration) can be varied in view of the observed effects of the administered therapeutic agents on the patient, and in view of the observed responses of the disease to the administered therapeutic agents.

EXAMPLES

Structure-Based Virtual Screening.

We docked 1323 FDA-approved drugs to the substrate binding site in FTO, and filtered the docking poses based on physicochemical descriptors, such as the number of hydrogen bonds, buried carbon atoms and hydrophobic contact. Then, the docking poses were minimized and rescored using more sophisticated scoring method. One top-ranked drug is entacapone (FIG. 1), which is a COMT (Catechol-O-methyltransferase) inhibitor used for treating Parkinson disease.

Enzymatic Inhibition.

Figure 2:
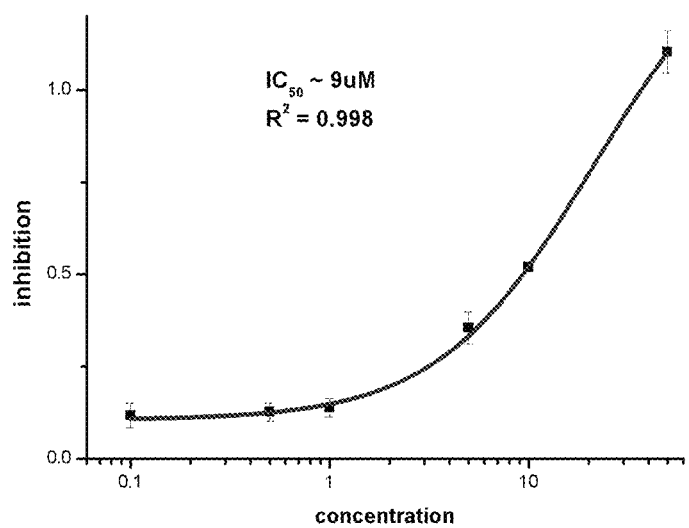
FIG. 2. The dose-dependent inhibition of entacapone against FTO protein measured in demethylation assay.

We measured the compound's inhibition activity in the demethylation reaction catalyzed by FTO. The assay was performed in 100 μl of reaction system containing 50 mM HEPES buffer (pH=7.0), 100 μM of a-KG, 100 μM of $(NH_4)_2Fe(SO_4)_2$, 1 mM of L-ascorbic acid, 50 μg/ml of BSA, 0.5 μM of ssDNA with $N^6$-mA (5'-ATTGTCA($m^6$A)CAGCAGA-3'), and 0.1 μM of FTO protein. The reaction system was incubated at 37° C. for 2 h and stopped by heating at 95° C. for 5 mM ssDNA was digested by nuclease P1 and alkaline phosphatase. The concentrations of $N^6$-mA and A were analyzed by HPLC-MS/MS. When concentration of substrate and enzyme are 0.5 μM and 0.1 μM, respectively, the measured $IC_{50}$ value of entacapone against FTO is ~9 μM (FIG. 2).

Cellular Triglyceride Synthesis Inhibition.

Figure 3:
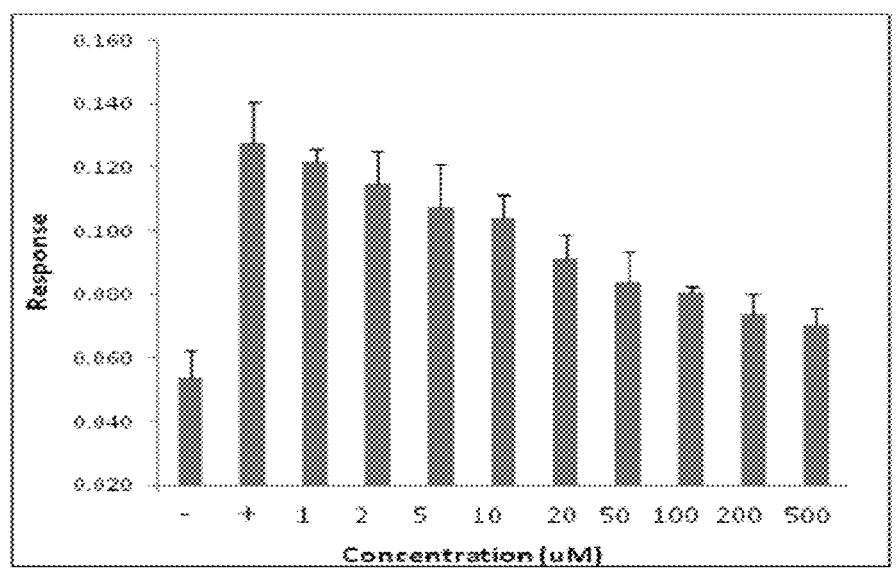
FIG. 3. The dose-dependent inhibition activity of entacapone on triglyceride synthesis in Huh-7 cell line. The X-axis is the compound concentration. The Y-axis is "read-out" of the triglyceride concentration using dyeing method.

We measured the compound's inhibition activity on triglyceride synthesis in Huh-7 cell line (FIG. 3), the $IC_{50}$ value of entacapone is ~15 uM.

In Vivo Anti-Obesity Efficacy.

Figure 4:
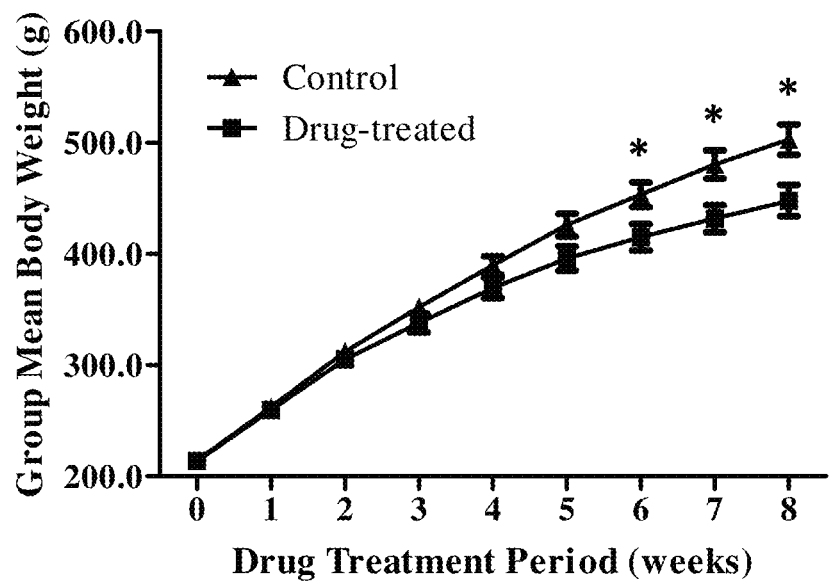
FIG. 4. Effects of entacapone on body weight in rats. (*p-value<0.05)
Figure 5:
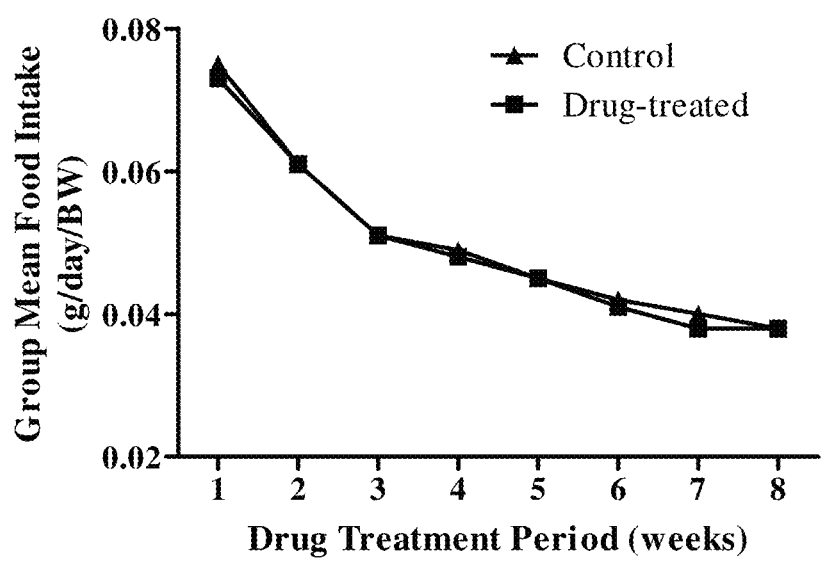
FIG. 5. Effects of entacapone on food intake in rats.
Figure 6:
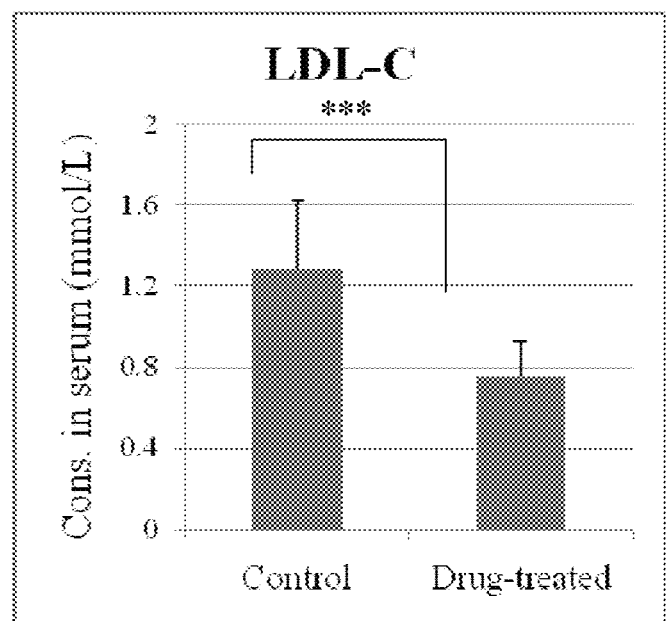
FIG. 6. Effects of entacapone on LDL-c of serum in rats. (***p-value<0.005)
Figure 7:
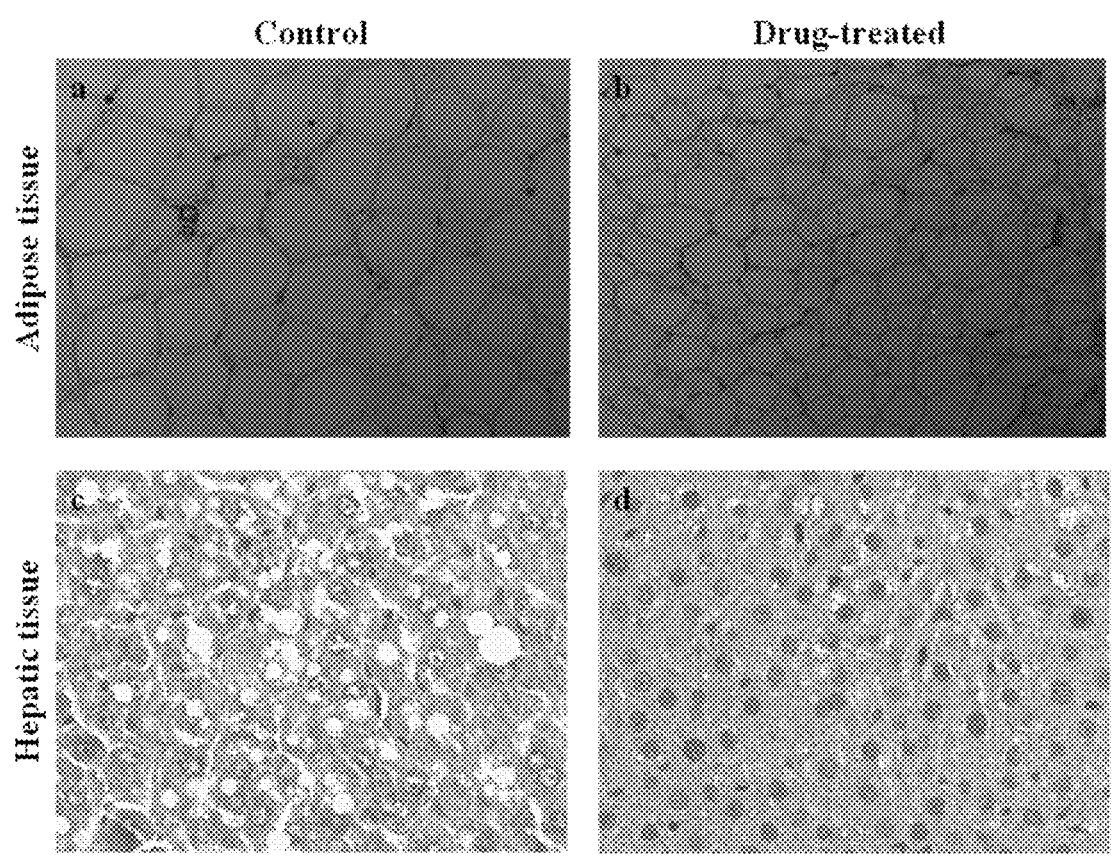
FIG. 7. Effects of entacapone on adipose and hepatic tissues in rats.

Total of 23 male wistar rats (6 weeks) were fed with high-fat diet (45% fat, OpenSource Diets D12451), and entacapone (85.6 mg/day) was administered to 12 randomly selected rats by gavage. After 8 weeks, the mean body weight of drug treatment group was about 11% less than that of control group (*p-value<0.05) (FIG. 4). However, the body-weight-normalized food intakes of the two groups showed no difference (FIG. 5). Interestingly, the LDL-c (Low Density Lipoprotein-cholesterol) in serum of drug treatment group decreased as about 40% comparing to that of control group (***p-value<0.005) (FIG. 6 and Table 1). The adipose and hepatic tissues of rat in drug-treated group showed dramatic changes comparing to control group, with reduced size of adipose cells and reduced level of liver steatosis (FIG. 7*a,b* H&E staining, 10× magnification; c,d H&E staining, 40× magnification).

TABLE 1

Effects of Entacapone on serum biochemistry in rats. Difference is the percentage of concentration change of index in drug treatment group compared to that in control group.

| Index | Difference | p-value |
|---|---|---|
| Cholesterol | −3.3% | 0.6455 |
| HDL-cholesterol | −0.026% | 0.9972 |
| LDL-cholesterol | −41.2% | 0.0005 |
| Triglyceride | −3.8% | 0.8023 |
| Bilirubin | −10.1% | 0.5814 |
| Albumin ratio | −0.063% | 0.9473 |
| Glutamic-pyruvic transaminase | −5.5% | 0.4962 |
| Creatine kinase | −17.6% | 0.2311 |

From these and other data we determined that anti-weight gain effective human dosages should be far in excess of the standard 200 mg/day dosage for treating Parkinsons, preferably 0.5-10, 0.5-5, 0.5-2.5, 0.5-1, 1-10, 1-5, 1-2.5, 2-10, or 2-5 g/day.

Figure 8:
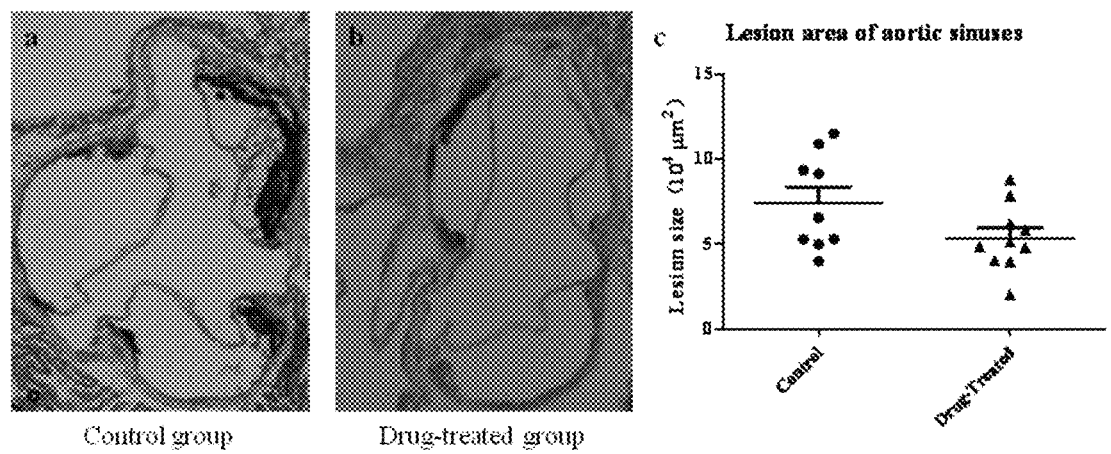
FIG. 8. The anti-atherosclerosis efficacy of entacapone in Ldlr-Deficient Mice. a and b. The Oil red O-stained lesion area in aortic sinuses of control group and drug-treated group, respectively. c. Quantitative analysis of lesional areas in the aortic sinuses of two groups.

Atherosclerosis Model:

Ldlr-Deficient Mice. We measured entacapone's anti-atherosclerosis efficacy using Ldlr$^{-/-}$ mice fed western style diet (20% fat, 0.15% cholesterol), entacapone (300 mg/day) was orally administered by blending with diet. After 8 weeks, the mean lesion area in aortic sinuses of drug treatment group was 28% less than that of control group (p-value=0.08) (FIG. 8). Therefore, entacapone reduces atherosclerosis symptom, comparing with the control.

In Vivo Anti-Obesity Efficacy in Obese Mice.

Figure 9:
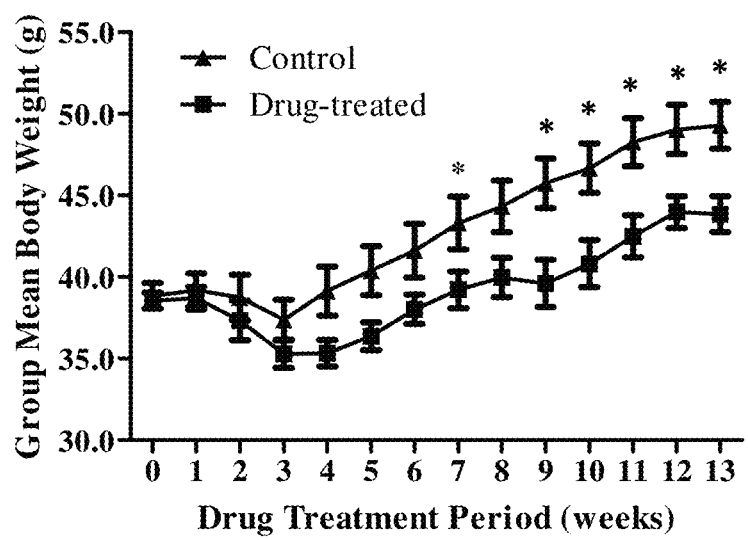
FIG. 9. Effects of entacapone on body weight in obese mice. (*p-value<0.05)

Male C57BL/6 mice were fed with high-fat diet (45% fat, OpenSource Diets D12451) for 8 weeks. Then obese mice with body weight 20% larger than that of mice fed with normal diet (20 mice) were selected for experiments. Entacapone (300 mg/kg) was orally administered to 10 randomly selected obese mice by blending with diet. After 13 weeks, the mean body weight gain of drug treatment group was about 11% less than that of control group (*p-value<0.05) (FIG. 9).

REFERENCES

1. Frayling, T. M. et al. A common variant in the FTO gene is associated with body mass index and predisposes to childhood and adult obesity. *Science* 316, 889-894, (2007).
2. Scuteri, A. et al. Genome-wide association scan shows genetic variants in the FTO gene are associated with obesity-related traits. *PLoS Genet* 3, e115, doi:07-PLGE-RA-0253 (2007).
3. Scott, L. J. et al. A genome-wide association study of type 2 diabetes in Finns detects multiple susceptibility variants. *Science* 316, 1341-1345, (2007).
4. Dina, C. et al. Variation in FTO contributes to childhood obesity and severe adult obesity. *Nat Genet* 39, 724-726, (2007).
5. Gao, X. et al. The fat mass and obesity associated gene FTO functions in the brain to regulate postnatal growth in mice. *PLoS One* 5, e14005, (2010).
6. Fischer, J. et al. Inactivation of the Fto gene protects from obesity. *Nature* 458, 894-898, (2009).
7. Church, C. et al. A mouse model for the metabolic effects of the human fat mass and obesity associated FTO gene. *PLoS Genet* 5, e1000599, (2009).
8. Church, C. et al. Overexpression of Fto leads to increased food intake and results in obesity. *Nat Genet* 42, 1086-1092, (2010).
9. Gerken, T. et al. The obesity-associated FTO gene encodes a 2-oxoglutarate-dependent nucleic acid demethylase. *Science* 318, 1469-1472 (2007).
10. Han, Z. et al. Crystal structure of the FTO protein reveals basis for its substrate specificity. *Nature* 464, 1205-1209, (2010).
11. Meyer, K. D. et al. Comprehensive Analysis of mRNA Methylation Reveals Enrichment in 3' UTRs and near Stop Codons. *Cell* 149, 1635-1646 (2012).
12. Jia, G. et al. N6-methyladenosine in nuclear RNA is a major substrate of the obesity-associated FTO. *Nat Chem Biol* 7, 885-887, (2011).

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein, including citations therein, are hereby incorporated by reference in their entirety for all purposes.

What is claimed is:

1. A method of treating obesity consisting of administering to an obese person diagnosed as in need thereof an effective amount of entacapone ((2E)-2-cyano-3-(3,4-dihydroxy-5-nitrophenyl)-N,N-diethylprop-2-enamide), or a pharmaceutically-acceptable salt thereof, and optionally, one or more pharmaceutically acceptable excipients, wherein the person has a body mass index (BMI) over 30, wherein the amount of entacapone or salt thereof is 0.5-5 g/day.

2. A The method of claim 1 wherein the person is determined to have a genotype having an Fto SNP that is SNP rs7202116 (G), rs1421085 (C), or rs9939609 (A), or a surrogate or proxy SNP in linkage disequilibrium therewith and having a $r^2$ value greater than 0.5.

3. A The method of claim 1 wherein the person is determined to over-expresses FTO or Fto.

4. A method of treating obesity consisting of administering to an obese person diagnosed as in need thereof an effective amount of entacapone ((2E)-2-cyano-3-(3,4-dihydroxy-5-nitrophenyl)-N,N-diethylprop-2-enamide), or a pharmaceutically-acceptable salt thereof, an effective amount of a second, different anti-obesity medicament, wherein the second, different anti-obesity medicament is a food intake inhibitor or a food absorption inhibitor or a reducer of serum LDL, cholesterol, LDL-c, or triglycerides, or a pharmaceutically-acceptable salt of said medicament, and optionally, one or more pharmaceutically acceptable excipients, wherein the person has a body mass index (BMI) over 30, wherein the amount of entacapone or salt thereof is 0.5-5 g/day.

5. The method of claim 4 wherein the person is determined to have a genotype having an Fto SNP that is SNP rs7202116 (G), rs1421085 (C), or rs9939609 (A), or a surrogate or proxy SNP in linkage disequilibrium therewith and having a $r^2$ value greater than 0.5.

6. The method of claim 4 wherein the person is determined to over-expresses FTO or Fto.

7. The method of claim 4 wherein said medicament is a food intake inhibitor or a food absorption inhibitor, and said medicament is Orlistat, Sibutramine, Lorcaserin, Rimonabant, Metformin, Exenatide, Pramlintide, or phentermine/topiramate.

8. The method of claim 5 wherein said medicament is a food intake inhibitor or a food absorption inhibitor, and said medicament is Orlistat, Sibutramine, Lorcaserin, Rimonabant, Metformin, Exenatide, Pramlintide, or phentermine/topiramate.

9. The method of claim 6 wherein said medicament is a food intake inhibitor or a food absorption inhibitor, and said medicament is Orlistat, Sibutramine, Lorcaserin, Rimonabant, Metformin, Exenatide, Pramlintide, or phentermine/topiramate.

10. The method of claim 4 wherein the medicament is a reducer of serum LDL, cholesterol, LDL-c, or triglycerides, and said medicament is a statin, cholestyramine (PREVALITE, QUESTRAN), colesevelam (WELCHOL), colestipol (COLESTID), ezetimibe (ZETIA), ezetimibe-simvastatin (VYTORIN), fenofibrate (LOFIBRA, TRICOR), gemfibrozil (LOPID), Niacin (NIASPAN), or Omega-3 fatty acid (LOVAZA).

11. The method of claim 5 wherein the medicament is a reducer of serum LDL, cholesterol, LDL-c, or triglycerides, and said medicament is a statin, cholestyramine (PREVALITE, QUESTRAN), colesevelam (WELCHOL), colestipol (COLESTID), ezetimibe (ZETIA), ezetimibe-simvastatin (VYTORIN), fenofibrate (LOFIBRA, TRICOR), gemfibrozil (LOPID), Niacin (NIASPAN), or Omega-3 fatty acid (LOVAZA).

12. The method of claim 6 wherein the medicament is a reducer of serum LDL, cholesterol, LDL-c, or triglycerides, and said medicament is a statin, cholestyramine (PREVALITE, QUESTRAN), colesevelam (WELCHOL), colestipol (COLESTID), ezetimibe (ZETIA), ezetimibe-simvastatin (VYTORIN), fenofibrate (LOFIBRA, TRICOR), gemfibrozil (LOPID), Niacin (NIASPAN), or Omega-3 fatty acid (LOVAZA).

13. The method of claim 4 the medicament is a reducer of serum LDL, cholesterol, LDL-c, or triglycerides, and said medicament is a statin, and said statin is atorvastatin (LIPITOR), fluvastatin (LESCOL), lovastatin (ALTOPREV, MEVACOR), pravastatin (PRAVACHOL), rosuvastatin (CRESTOR), or simvastatin (ZOCOR).

14. The method of claim 5 the medicament is a reducer of serum LDL, cholesterol, LDL-c, or triglycerides, and said medicament is a statin, and said statin is atorvastatin (LIP- ITOR), fluvastatin (LESCOL), lovastatin (ALTOPREV, MEVACOR), pravastatin (PRAVACHOL), rosuvastatin (CRESTOR), or simvastatin (ZOCOR).

15. The method of claim 6 the medicament is a reducer of serum LDL, cholesterol, LDL-c, or triglycerides, and said medicament is a statin, and said statin is atorvastatin (LIPITOR), fluvastatin (LESCOL), lovastatin (ALTOPREV, MEVACOR), pravastatin (PRAVACHOL), rosuvastatin (CRESTOR), or simvastatin (ZOCOR).

* * * * *